United States Patent [19]

Luhr et al.

[11] Patent Number: 5,372,598
[45] Date of Patent: Dec. 13, 1994

[54] SMALL BONE PLATE FOR CRANIAL OR FACIAL FRACTURES OR THE LIKE

[75] Inventors: Hans-Georg Luhr, Göttingen; Hans E. Harder, Probsteigerhagen, both of Germany

[73] Assignee: Howmedica GmbH, Schoenkirchen, Germany

[21] Appl. No.: 883,808

[22] Filed: May 14, 1992

Related U.S. Application Data

[63] Continuation of Ser. No. 758,537, Sep. 9, 1991, abandoned, which is a continuation of Ser. No. 614,953, Nov. 15, 1990, abandoned, which is a continuation of Ser. No. 192,738, May 11, 1988, abandoned.

[30] Foreign Application Priority Data

May 14, 1987 [DE] Germany ............... 68706912
Feb. 6, 1988 [DE] Germany ............... 88101736

[51] Int. Cl.$^5$ ........................................... A61B 17/56
[52] U.S. Cl. ........................................ 606/69; 606/71
[58] Field of Search ............................ 606/69-77

[56] References Cited

U.S. PATENT DOCUMENTS

| | | | |
|---|---|---|---|
| 1,105,105 | 7/1914 | Sherman | 128/924 P |
| 2,494,229 | 1/1950 | Collison | 606/69 |
| 3,547,114 | 12/1970 | Haboush | 606/71 |
| 3,779,240 | 12/1973 | Kondo | 606/69 |
| 4,219,015 | 8/1980 | Steinemann | 606/69 |
| 4,503,848 | 3/1985 | Caspar et al. | 128/924 P |
| 4,683,878 | 8/1987 | Carter | 606/69 |
| 4,905,679 | 3/1990 | Morgan | 606/70 |
| 4,905,680 | 3/1990 | Tunc | 606/69 |

FOREIGN PATENT DOCUMENTS

| | | | |
|---|---|---|---|
| 2806609 | 7/1979 | Germany | 128/92 YL |
| 8528003 | 2/1986 | Germany . | |

OTHER PUBLICATIONS

Hans G. Luhr, M.D., D.M.D., "Indications for Use of a Microsystem for Internal Fixation in Craniofacial Surgery", J. of Craniofacial Surgery, vol. 1, No. 1, Jan., 1990, pp. 35–52.

Primary Examiner—Michael A. Brown
Attorney, Agent, or Firm—Peter C. Richardson; Lawrence C. Akers; Elizabeth O. Slade

[57] ABSTRACT

A small bone plate suitable for use, for example, on the cranial skeleton, on the facial skeleton and on micro fragments of other skeleton sections is provided. The bone plate is formed from webs joining screw hole boundaries in a particular fashion; and the plate can be bent in its plane, without deformation of the screw hole boundaries. Thus, insertion of bone screws into the small bone plate is not hindered by deformed screw hole boundaries. The bone plate can be single-legged or multiple-legged. Also provided is a special type of bone screw especially suitable for use with the small bone plate of the invention. The bone screw has a cross-slotted head, with the bottoms of the slots being concave. The screw is also preferably self-tapping and preferably has a conical tip.

13 Claims, 2 Drawing Sheets

SMALL BONE PLATE FOR CRANIAL OR FACIAL FRACTURES OR THE LIKE

This application is a continuation of 07/758,537, filed Sep. 9, 1991, now abandoned, which is a continuation of 07/614,953, filed Nov. 15, 1990, now abandoned, which is a continuation of 07/192,738, filed May 11, 1988, now abandoned.

BACKGROUND OF THE INVENTION

The invention relates to a bone plate, in particular for the application to fractures of the cranial and facial skeletons.

Such bone plates are shown in German Petty Patent 8528003 for instance. They consist of a physically compatible material such as e.g. titanium or a chromium cobalt molybdenum alloy. The relatively thin plates are strip-like in shape and provided with spaced-apart holes for receiving bone screws. They are designed such that they are deformable by the surgeon in order to conform to the bone in the region of application. It is also known to provide diminished webs located between the screw holes and having a cross-sectional area such that the cross-sectional area of the web is smaller than twice the cross-sectional area of the hole boundary. Thereby it is to be ensured that upon bending of the bone plate, in particular in its plane, the hole boundary is not bent. Rather, the bending resistance in the region of the webs is to be smaller than in the region of the screw hole boundary, so that substantially only bending of the webs occurs. It has been found, however, that on the one hand the webs must have a certain minimum strength and that on the other hand the width of the plates in the region of the screw hole boundary must not exceed certain values. There is therefore still the danger that upon bending of the bone plates, in particular such with very small dimensions, the screw hole boundary is also deformed.

OBJECTS OF THE INVENTION

Hence the object of the invention is to provide a bone plate, in particular for the application to fractures of the cranial and facial skeleton or the like, which permits slight bending of the plates in their plane, without causing a noticeable deformation of the screw hole boundaries.

The object is solved by the bone plate of the invention.

SUMMARY OF THE INVENTION

The inventor has realized that a very small radius is to be selected for the transition from the web to the screw hole boundary. Theoretically the most favorable transition would be one wherein the sides of the webs extend approximately at right angles to the screw hole boundary. With such transition, essentially no force transmission occurs from the web to the hole boundary when the plate is bent in its plane. Such right angles are difficult to manufacture and also undesirable due to their notch effect. In any case, intended is a very small radius which for instance is about 0.5 or smaller when the web width is 1.0 to 1.5 mm and the plate thickness is 0.7 mm. With a still smaller plate which has a web width of 0.5 to 0.7 mm said radius is 0.3 mm or smaller.

With the bone plate according to the present invention, owing to its design, upon bending of the bone plate in its plane the screw hole boundary is prevented from being noticeably affected, and the danger of fit deterioration of the screw head is prevented. In prior bone plates, deformation of the screw hole boundary can reach such an extent that insertion of the screw is impossible.

Prior bone plates are comprised of a plurality of legs which are arranged at angles with respect to each other, e.g. L-shaped, T- or double T-shaped bone plates. In this connection, an embodiment of the invention provides that a leg is provided with approximately parallel side edges and, through a diminished web, merges into the hole boundary of an adjacent leg. In this embodiment, the one leg has over a great part of its length a constant width which corresponds to the outer diameter of the screw hole boundary. Such bone plate portion is therefore relatively stable, whereas the remaining portions are deformable between the screw hole boundaries in accordance with the present invention. Thus the stable portion serves as static element for joining fractural segments, while the remaining bone plate portions permit a more easy deformation by the surgeon. So, they are necessarily also more or less dynamic.

Some sections of the facial skeleton have extremely little covering by soft parts. The bone plates described for the application to fractures of the facial skeleton are for longtime implantation. Conventional plates are dimensioned such that they cause visible elevations in the area attended to. To provide a remedy here, a further embodiment of the invention provides that the bone plate has a thickness of 0.4 to 0.7 mm and a web width of 0.5 to 0.8 mm, preferably 0.6 mm. The outer diameter of the hole boundary is preferably 2 to 2.4 mm, in particular 2.2 mm. This provides for an ossicle plate which is dimensioned so small that it is not at all or hardly visible in the implanted state and is also inconspicuous under a thin soft-part covering.

Bone plates are normally fixed to the bone fragments with screws. To ensure an adequately strong fit in the bone, the screw spacings must not be too small. An embodiment of the present invention therefore provides that the spacing between the holes is between 3.5 and 5 mm. Thus, in proportion a relatively long web is comparatively easily deformable and conformable to the individual bone contour by the surgeon during the operation.

The bone plate according to the present invention, in particular the small bone plate, is not restricted to the use in the area of the cranial and facial skeleton of adults or babies but also micro fragments of other skeleton sections are fixable therewith.

The screws used to fix the bone plates normally have a countersunk head cooperating with a countersinking of the screw holes. The screws are naturally comparatively small and therefore correspondingly intricate to handle. An embodiment of the present invention provides that the screw is a recessed oval-head countersunk screw, with the bottom of the slots being concave. The use of recessed head screws for ossicle plates is known per se. With the so-called Philips design, the slots do not extend beyond the peripheral surface of the head. A certain centering effect is obtained thereby. Disadvantageous in such cross recess is, however, that the slots extend deep into the stem which, in particular when the diameters are very small, is undesirably drastically weakened. Moreover, a Philips-type head must be of relatively large volume, which is also disadvantageous in very small bone plates. With the other cross recess design, the so-called Sherman design, the slots extend beyond the peripheral surface, which involves a corresponding weakening of the screw head. Above all, there is the danger of the screw-driver disengaging from the head upon tilting of the screw. In the screw according to the present invention, the bottom of the slots is concave. This admittedly entails a slightly more weakened head than the head of the Philips design, but the weakening does not go so far as with the Sherman design, as the slots and, respectively, the curvature of the bottom thereof are selectable such that they can emerge from the head above the countersinking. Thus, the head obtained is only slightly weakened, but of a relatively small volume and has an outer surface which must be only relatively insignificantly curved. Above all, a great advantage consists in the fact that owing to the specific design of the cross recess a self-centering feature occurs upon engagement by the screw-driver. The latter is, according to a further embodiment of the invention, preferably concave at the ends in accord with the curvature of the slot bottom.

The self-tapping threaded screw used with ossicle plates has, according to a further embodiment of the present invention, a diameter of 0.5 to 0.8 mm, the head having a diameter of about 1.6 mm. The concavity of the slot bottom has a radius of about 1.5 mm, whereas the convexity of the head has a radius of about 2 mm.

The bone screw described does not, however, have a metric thread, corresponding to the 0.8 mm diameter, but has a pitch of 0.25 to 0.35 mm, which corresponds to the pitch of a M1 thread in the case of 0.25. Further, according to the present invention, it is provided that the core diameter is only about 0.4 mm. This yields a thread which ensures a tight and reliable fit in the bone. In particular the relatively great thread depth yields an effective anchorage in the bone.

The self-tapping feature is achieved in the prior screws through one or two diametrically opposite milled grooves which are cut in approximately axially parallel relationship in the area of the screw tip.

In addition, an embodiment of the present invention provides that reductions converging towards the tip are provided at opposite sides of the threaded stem near the tip. In the region of the reductions produced by grinding the threads are removed. They remain in the remaining portion. Such design ensures adequate tapping properties, so that upon a corresponding axial pressure the threaded screw is easily and effectively screwable into the bone without predrilling of a hole. To effect initial penetration of the screw, an embodiment of the present invention requires that a conical tip, preferably at an angle of about 60°, is provided.

BRIEF DESCRIPTION OF THE DRAWINGS

The invention will now be explained in greater detail with reference to the accompanying drawings in which.

Figure 1:
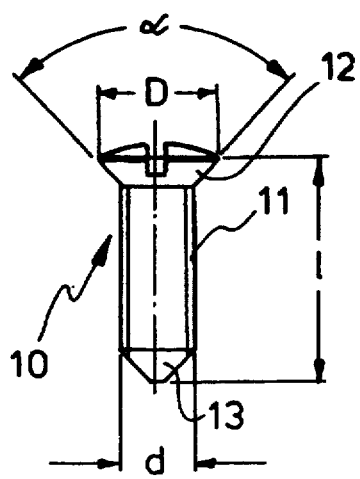
FIG. 1 shows a schematic view of a bone screw for bone plates according to the invention.

Before describing the details illustrated in the drawings, it is premised that every described feature is of significance to the invention per se or in conjunction with features of the claims.

DETAILED DESCRIPTION OF THE DRAWINGS

Figure 2:
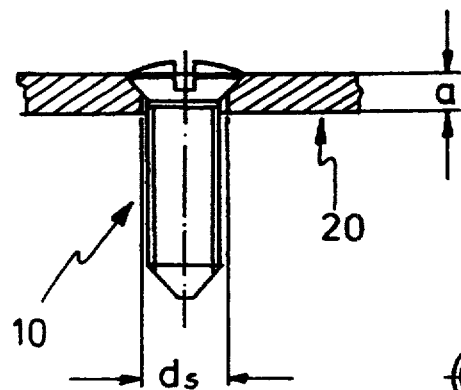
FIG. 2 shows the screw of FIG. 1 in connection with a bone plate.

The bone screw 10 depicted in FIGS. 1 and 2 possesses a threaded stem 11, a head 12 and a tip 13. The diameter d of the threaded stem 11 is e.g. 0.8 mm. The head 12 is an oval countersunk head with a countersinking at an angle of $\alpha = 90°$. The diameter D of the head is about 1.6 mm. Further details of the screw 10 will be described in conjunction with FIG. 5.

Figure 3:
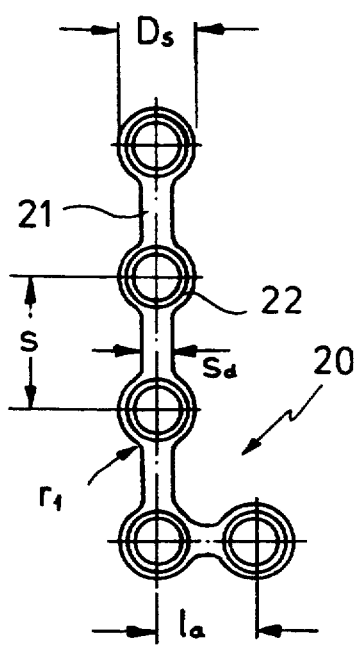
FIG. 3 shows a top view of a first embodiment of a bone plate according to the invention.

FIG. 3 shows an L-shaped bone plate 20. It is composed of individual webs 21 between which a screw hole boundary 22 is arranged. The screw hole boundaries have a spacing S of about 3.5 mm therebetween. The webs have a thickness of $S_1$ of about 0.6 mm. The outer diameter of the screw hole boundary $D_S$ is about 2.2 mm. The inner diameter $d_s$ is about 1.2 mm. FIG. 2 shows the cross-section of the plate 20. The thickness thereof is about 0.4 to 0.5 mm. It is apparent that the cross-sectional surface of the webs 21 is smaller than twice the cross-sectional surface of the hole boundary 22. With a bent leg, the spacings between the holes are respectively 2.5 and 4 mm. Further, it is essential to point out that the radius $r_1$ between the web 21 and the hole boundary 22, i.e. the rounded transition between the outer sides of the webs 21 and the hole boundary 22 is 0.3 mm or less.

Figure 4:
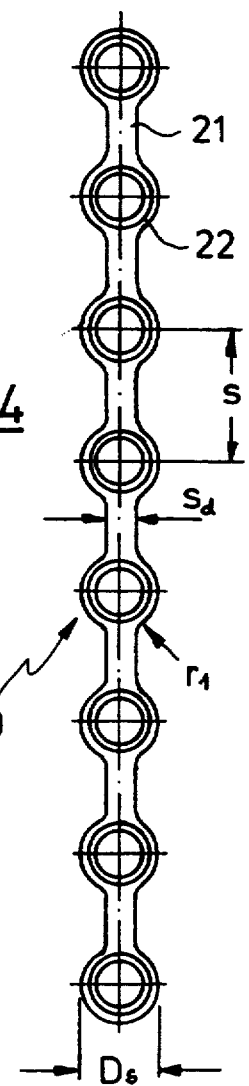
FIG. 4 shows a top view of a second embodiment of a bone plate according to the invention.

The dimensions of the ossicle plate 30 of FIG. 4 correspond to those of FIG. 3, so that no detailed description thereof is required. The bone plate 30 is a individual longer strip with a series of webs 21 and hole boundaries 22.

Figure 6:
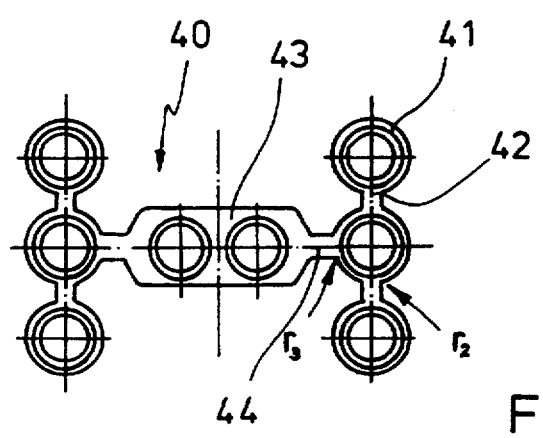
FIG. 6 shows a third embodiment of a bone plate according to the invention.

A bone plate 40 according to FIG. 6 has slightly larger dimensions. The outer diameter of the hole boundary 41 is about 5 mm. The thinner webs 42 between the screw hole boundaries 41 have a width of 1 to 1.5 mm. The bone plate 40 is a double-T plate, the central web 43 thereof being of uniform width over most of its length, i.e. being not diminished between the screw hole boundaries. The central web 43 merges into reduced narrower webs 44 of a width of about 1.5 mm into the adjacent screw hole boundaries 41. The thickness of the plate 40 is about 0.7 mm. The central portion of the central web 43 is therefore relatively stable and is not likewise deformed upon deformation of the remaining plate portions. The respective webs 42 and 44 also merge into the screw hole boundaries 41 at a very small respective radius $r_2$ and $r_3$ of about 0.5 mm.

The two embodiments shown in FIGS. 2 and 3 and 6 respectively show the webs between the screw hole boundaries to be approximately at angles with the screw hole boundaries in the joining region.

Figure 5:
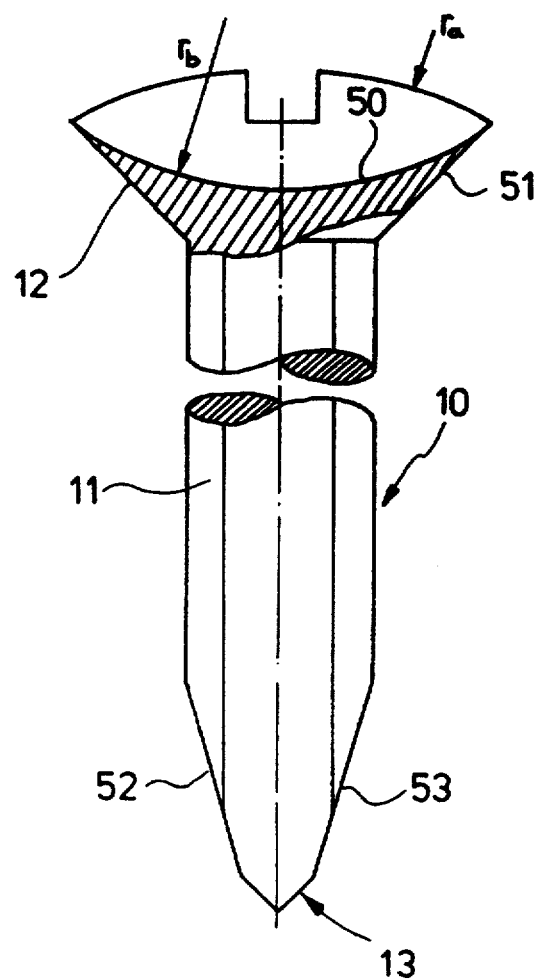
FIG. 5 is an enlarged view of the screw of FIG. 1.

The enlarged screw 10 of FIG. 5 is provided with a cross recess which has a concave bottom 50. The curvature is selected such that the countersunk peripheral surface 51 is not transgressed. The radius of the bottom $r_b$ is e.g. 1.5 mm. The radius $r_a$ of the oval head 12 is e.g. 2 mm. The slot width is 0.3 mm.

The tip 13 is conically chamfered at an angle of 60°. Adjacent to said tip at opposite sides are reductions 52,53 which have no thread in their area. The reductions 52,53 and also the tip 13 are formed by grinding. The reductions 52,53 ensure the self-tapping feature of the screw 10.

The members described are made of a physically compatible material, in particular a chromium cobalt molybdenum alloy.

It should also be mentioned that the pitch of the thread of the screw 10 is 0.25, that the thread has a flank angle of 60°, and that the core diameter is about 0.4 mm.

We claim:

1. A bone plate which is substantially planar, which lies in a plane P, and which is for use on fractures and osteotomies of a cranial and facial skeleton and micro fragments of other skeleton sections, comprising screw hole boundaries for receiving bone screws and diminished webs between the screw hole boundaries, at least part of the webs having a cross-sectional area which is at most twice the cross-sectional area of the screw hole boundary, the webs merging into the screw boundaries in transitions which are of circular arc fashion and of radius r, wherein said radius r of the transition from the web (21) to the screw hole boundary (22) is dimensioned to be so small that upon bending of the bone plate in plane P such that adjacent hole boundaries contact each other, essentially only the webs (21) are deformed, wherein said web has a width of about 1.0 to 1.5 mm and a thickness of about 0.7 mm, and said radius r is at most about 0.5 mm.

2. A bone plate according to claim 1, wherein said bone plate has a thickness of 0.4 to 0.7 mm and a web width of 0.5 to 0.8 mm.

3. A bone plate according to claim 2, wherein the adjacent holes are spaced apart 3.5 to 5.0 mm and wherein the web width is 0.6 mm.

4. A bone plate according to claim 1, and including also at least one recessed counter-sunk screw (10) having an oval-shaped head, wherein said head of said screw is slotted with slots having concave-shaped bottoms (50).

5. A bone plate according to claim 4, wherein said screw has a stem (11) which is self-tapping and threaded and having a diameter of about 0.8 mm, and wherein said screw has a head having a diameter of 1.6 mm.

6. A bone plate according to claim 5, wherein said stem is threaded with a thread with a diameter of about 0.8 mm and a pitch of 0.25 to 0.35.

7. A bone plate according to claim 4, wherein said slots having concave-shaped bottoms have a concavity with a radius of about 1.5 mm and wherein said head has a convexity with a radius of about 2 mm.

8. A bone plate according to claim 4, wherein said screw (10) has an inner thread diameter of about 0.4 mm.

9. A bone plate according to claim 4, wherein said at least one screw (10) has a stem (11) which is self-tapping and threaded and wherein said stem has a tip having reductions (52, 53) located on opposite sides of said stem.

10. A bone plate according to claim 9, wherein said bone screw has a conical tip (13), with a flank angle of about 60°.

11. A bone plate which is substantially planar, which lies in a plane P, and which is for use on fractures and osteotomies of a cranial and facial skeleton and micro fragments of other skeleton sections, comprising screw hole boundaries for receiving bone screws and diminished webs between the screw hole boundaries, at least part of the webs having a cross-sectional area which is at most twice the cross-sectional area of the screw hole boundary, the webs merging into the screw hole boundaries in transitions which are of circular arc fashion and of radius r, wherein said radius r of the transition from the web (21) to the screw hole boundary (22) is dimensioned to be so small that upon bending of the bone plate in plane P such that adjacent hole boundaries contact each other, essentially only the webs (21) are deformed, wherein two or more legs are arranged at nonzero angles with respect to each other, and wherein a leg (43) is provided with approximately parallel side edges and merges via a diminished web (44) into a screw hole boundary (41) of an adjacent leg.

12. A bone plate which is substantially planar, which lies in a plane P, and which is for use on fractures and osteotomies of a cranial and facial skeleton and micro fragments of other skeleton sections, comprising screw hole boundaries for receiving bone screws and diminished webs between the screw hole boundaries, at least part of the webs having a cross-sectional area which is at most twice the cross-sectional area of the screw hold boundary, said webs having an outer edge and said screw hole boundaries having an outer edge, the webs merging into the screw hole boundaries in transitions which are of circular arc fashion and of radius r, wherein said radius r of the transition from the web (21) to the screw hole boundary (22) is dimensioned to be so small that upon bending of the bone plate in plane P such that adjacent hole boundaries contact each other, essentially only the webs (21) are deformed, wherein said webs intersect said screw hole boundaries such that said outer edges of the webs intersect said outer edges of the screw hole boundaries at angles that are only slightly greater than 90°.

13. A bone plate which is substantially planar, which lies in a plane P, and which is for use on fractures and osteotomies of a cranial and facial skeleton and micro fragments of other skeleton sections, comprising screw hole boundaries for receiving bone screws and diminished webs between the screw hole boundaries, at least part of the webs having a cross-sectional area which is at most twice the cross-sectional area of the screw hole boundary, the webs merging into the screw boundaries in transitions which are of circular arc fashion and of radius r, wherein said radius r of the transition from the web (21) to the screw hole boundary (22) is dimensioned to be so small that upon bending of the bone plate in plane P such that adjacent hole boundaries contact each other, essentially only the webs (21) are deformed, wherein said web has a width of about 0.5 mm to 0.8 mm and a thickness of about 0.4 mm to 0.7 mm, and said radius r is at most about 0.3 mm.

* * * * *